United States Patent
Mann

(10) Patent No.: US 9,930,891 B2
(45) Date of Patent: Apr. 3, 2018

(54) SYNERGISTIC HERBICIDAL COMPOSITION CONTAINING PENOXSULAM AND PYROXSULAM

(75) Inventor: Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/420,695

(22) Filed: Mar. 15, 2012

(65) Prior Publication Data

US 2012/0238449 A1 Sep. 20, 2012

Related U.S. Application Data

(60) Provisional application No. 61/453,202, filed on Mar. 16, 2011.

(51) Int. Cl.

| | |
|---|---|
| *A01N 43/60* | (2006.01) |
| *A01P 13/00* | (2006.01) |
| *A01N 43/90* | (2006.01) |
| *A01N 43/28* | (2006.01) |
| *A01N 43/713* | (2006.01) |
| *A01N 43/653* | (2006.01) |
| *A01N 41/06* | (2006.01) |
| *A01N 43/40* | (2006.01) |

(52) U.S. Cl.
CPC ............ *A01N 43/90* (2013.01); *A01N 41/06* (2013.01); *A01N 43/28* (2013.01); *A01N 43/40* (2013.01); *A01N 43/653* (2013.01); *A01N 43/713* (2013.01)

(58) Field of Classification Search
CPC ...... A01N 43/90; A01N 43/653; A01N 41/06; A01N 43/713; A01N 43/40; A01N 43/28
See application file for complete search history.

(56) References Cited

U.S. PATENT DOCUMENTS

| | | |
|---|---|---|
| 5,858,924 A | 1/1999 | Johnson et al. |
| 6,559,101 B2 | 5/2003 | Johnson et al. |
| 2009/0062121 A1* | 3/2009 | Satchivi et al. .............. 504/105 |
| 2010/0279864 A1 | 4/2010 | Mann et al. |
| 2010/0311588 A1* | 12/2010 | Gatzweiler et al. .......... 504/133 |
| 2011/0190136 A1 | 8/2011 | Hufnagl et al. |

FOREIGN PATENT DOCUMENTS

| | | | |
|---|---|---|---|
| WO | WO 2009/019431 | * 2/2009 | ............ A01N 41/10 |
| WO | 2010126812 A1 | 11/2010 | |

OTHER PUBLICATIONS

Disclosed Anonymously 462055: "2-(2,2-difluoroethoxy)-6-trifluoromethyl-N-(5,8-dimethoxy[1,2,4]triazolo[1,5-c]pyrimidin-2-yl)benzenesulfonamide and its use as a herbicide in mixtures" Research Disclosure, Oct. 2002, pp. 1832-1833.
"Penoxsulam and Its Use as a Herbicide in Mixtures for Use in Rice, Wheat, Barely, Oats, Sorghum, Corn, Maize, Ivm, Rangeland Pastures, Grasslands, Fallowland, Turf, and Aquatics" The IP.com Journal, vol. 5, No. 4, Apr. 2005, pp. 286-293.
Disclosed Anonymously 459085: "N-(5,7-Dimethoxy[1,2,4]Triazolo[1,5-a]Pyrimidin-2-YL)Arylsulfonamide Compounds and Their Use as Herbicides in Mixtures" Research Disclosure, Jul. 2002, pp. 1230-1231.

* cited by examiner

*Primary Examiner* — Mina Haghighatian
*Assistant Examiner* — Mei Ping Chui
(74) *Attorney, Agent, or Firm* — Michael R. Asam

(57) ABSTRACT

A synergistic mixture of penoxsulam and pyroxsulam controls weeds in rice, cereal and grain crops, tree and vine crops, pome, stone and citrus crops, pastures, rangelands, industrial vegetation management (IVM), and turf.

4 Claims, No Drawings

SYNERGISTIC HERBICIDAL COMPOSITION CONTAINING PENOXSULAM AND PYROXSULAM

CROSS REFERENCE TO RELATED APPLICATIONS

This application claims the benefit of U.S. Provisional Patent Application Ser. No. 61/453,202 filed Mar. 16, 2011.

FIELD OF THE INVENTION

This invention concerns a synergistic herbicidal composition containing (a) penoxsulam and (b) pyroxsulam for controlling weeds, especially in rice, cereal and grain crops, tree and vine crops, pome, stone and citrus crops, pastures, rangelands, industrial vegetation management (IVM), and turf.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429 "'synergism' [is] an interaction of two or more factors such that the effect when combined is greater than the predicted effect based on the response to each factor applied separately." The present invention is based on the discovery that penoxsulam and pyroxsulam, already known individually for their herbicidal efficacy, display a synergistic effect when applied in combination.

SUMMARY OF THE INVENTION

The present invention concerns a synergistic herbicidal mixture comprising an herbicidally effective amount of (a) penoxsulam and (b) pyroxsulam. The compositions may also contain an agriculturally acceptable adjuvant and/or carrier.

The present invention also concerns herbicidal compositions for and methods of controlling the growth of undesirable vegetation, particularly in rice, cereal and grain crops, tree and vine crops, pome, stone and citrus crops, pastures, rangelands, industrial vegetation management (IVM), and turf, and the use of these synergistic compositions.

The species spectra of penoxsulam and pyroxsulam, i.e., the weed species which the respective compounds control, are broad and highly complementary. It has now been found that a combination of penoxsulam and pyroxsulam exhibits a synergistic action in the control of wild oat (*Avena fatua*, AVEFA); Shepherds purse (*Capsella bursa-pastoris*, CAPBP); common lambsquarter (*Chenopodium album*, CHEAL); barnyardgrass (*Echinochloa crus-galli*, ECHCG); ryegrass (*Lolium* spp., LOLSS); short-spiked canarygrass (*Phalaris brachystachys*, PHABR); awned canarygrass (*Phalaris paradoxa*, PHAPA); narrow-leaved plantain (*Plantago lanceolata*, PLALA); annual blackgrass (*Poa annua*, POAAN); and wild buckwheat (*Polygonum convolvulus*, POLCO).

DETAILED DESCRIPTION OF THE INVENTION

Penoxsulam is the common name for 2-(2,2-difluoroethoxy)-N-(5,8-dimethoxy-[1,2,4]triazolo[1,5-c]pyrimidin-2-yl)-6-(trifluoromethyl)benzenesulfonamide. Its herbicidal activity is described in *The Pesticide Manual*, Fifteenth Edition, 2009. Penoxsulam controls *Echinochloa* spp., as well as many broadleaf, sedge and aquatic weeds in rice, and *Apera* spp. grass in cereals, as well as many broadleaf weeds in aquatics, many cereal crops, range and pasture, IVM and turf.

Pyroxsulam, N-(5,7-dimethoxy[1,2,4]triazolo[1,5-a]pyrimidin-2-yl)-2-methoxy-4-(trifluoromethyl)-3-pyridinesulfonamide, is a triazolopyrimidine sulfonamide herbicide, and its herbicidal activity is described in *The Pesticide Manual*, Fifteenth Edition, 2009. Pyroxsulam provides broad-spectrum, post-emergence annual grass and broadleaf weed control in cereals.

The term herbicide is used herein to mean an active ingredient that kills, controls or otherwise adversely modifies the growth of plants. An herbicidally effective or vegetation-controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant, to the locus of the plant at any stage of growth or before planting or emergence or after emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of penoxsulam to pyroxsulam at which the herbicidal effect is synergistic lies within the range of from about 1:15 to about 20:1. The rate at which the synergistic composition is applied will depend upon the particular type of weed to be controlled, the degree of control required, and the timing and method of application. In general, the composition of the invention can be applied at an application rate from about 9 grams per hectare (g/ha) to about 140 g/ha based on the total amount of active ingredients in the composition. Penoxsulam is applied at a rate from about 4 g/ha to about 80 g/ha and pyroxsulam is applied at a rate from about 5 g/ha to about 60 g/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the synergistic composition of the present invention include: 2,4-D esters and amines, acetochlor, acifluorfen, aclonifen, alachlor, ametryn, amidosulfuron, aminocyclopyrachlor, aminopyralid, aminotriazole, amitrol, ammonium thiocyanate, anilifos, asulam, atrazine, azimsulfuron, beflubutamid, benazolin, benefin, benfuresate, bensulfuron, bensulide, bentazon, benthiocarb, benzobicyclon, benzofenap, bifenox, bispyribac, bromacil, bromobutide, bromoxynil, butachlor, butafenacil, butralin, cafenstrole, carbetamide, carfentrazone-ethyl, chlorflurenol, chlorimuron, chlormequat, chlorpropham, chlortoluron, cinidon-ethyl, cinosulfuron, clethodim, clodinafop-propargyl, clomazone, clomeprop, clopyralid, cloransulam, cumyluron, cyanazine, cyclosulfamuron, cycloxydim, cyhalofop, daimuron, dicamba, dichlobenil, dichlorprop, diclofop-methyl, diclosulam, diflufenican, diflufenzopyr, dimefuron, dimepiperate, dimethametryn, dimethenamid, dimethenamid, diquat, dithiopyr, diuron, EK2612, EPTC, erioglaucine, esprocarb, ET-751, ethofumesate, ethoxysulfuron, ethbenzamide, etobenzanid, F7967, fenoxaprop-p-ethyl, fenoxaprop-p-ethyl+isoxadifen-ethyl, fenoxasulfone (KIH-071), fentrazamide, flazasulfuron, florasulam, fluazifop, flucarbazone, flucetosulfuron, flufenacet, flufenpyr, flumetsulam, flumiclorac, flumioxazin, fluometuron, flupyrsulfuron, fluroxypyr, flurtamone, fosamine, fomesafen, foramsulfuron, fumiclorac, glufosinate, glyphosate, halosulfuron, haloxyfop, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, ipfencarbazone (HOK-201), IR 5790, isoproturon, isoxaben, isoxaflutole, lactofen, linuron, MCPA esters and amines, mecoprop-P, mefenacet, mesosulfuron, mesosulfuron-ethyl sodium, mesotrione, metamifop, metazosulfuron (NC-620), metolachlor, metosulam, metribuzin, metsulfuron, metsulfuron-methyl, molinate, monosulfuron, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, pentoxazone, pethoxamid, picloram, picolinafen, pinoxaden, piperophos, pretilachlor, primisulfuron-methyl, prodiamine, profluazol, profoxydim, prohexadione, prometon, pronamide, propachlor, propanil, propisochlor, propoxycarbazone, propyrisulfuron (TH-547), propyzamide, prosulfocarb, prosulfuron, pyrabuticarb, pyraclonil, pyraflufen-ethyl, pyrazogyl, pyrazolynate, pyrazosulfuron-ethyl, pyrazoxyfen, pyribenzoxim, pyridate, pyriftalid, pyriminobac, pyrimisulfan (KUH-021), pyrithiobac, pyroxasulfone (KIH-485), quinclorac, quinmerac, quinoclamine, quizalofop, rimsulfuron, S-3252, saflufenacil, sethoxydim, simazine, simetryne, SL-0401, SL-0402, sulcotrione, sulfentrazone, sulfometuron, sulfosate, sulfosulfuron, tebuthiuron, tefuryltrione (AVH-301), tembotrione (AE0172747), terbacil, thenylchlor, thiazopyr, thiencarbazone, thifensulfuron, thifensulfuron-methyl, thiobencarb, topramezone, tralkoxydim, triasulfuron, tribenuron, tribenuron-methyl, triclopyr, trifloxysulfuron, trifluralin, trinexapac, tritosulfuron and salts, esters, optically active isomers and mixtures thereof.

The synergistic composition of the present invention can, further, be used in conjunction with glyphosate, glufosinate, dicamba, imidazolinones, sulfonylureas, or 2,4-D on glyphosate-tolerant, glufosinate-tolerant, dicamba-tolerant, imidazolinone-tolerant, sulfonylurea-tolerant and 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.1 to 98 percent by weight. Concentrations from 10 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before making a postemergence, foliar application to exposed weed and crop foliage, or applied as a dry or liquid formulation directly into flooded rice fields. The diluted compositions usually applied as a postemergence, foliar application to weeds or the locus of weeds generally contain 0.001 to 20 weight percent active ingredient and preferably contain 0.002 to 10 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention.

These trials were conducted under field conditions in France, Poland and Syria. Trial sites were located in commercially grown crops wheat, barley and corn. The crops were grown using normal cultural practices for fertilization, seeding, and maintenance to ensure good growth of the crop and the weeds. The trials were conducted using typical small plot herbicide research methodology. Trial plots were between 1 to 2.5 meters (m) wide by 6 to 42 m long. All treatments were applied using a randomized complete block trial design with 2 to 4 replications per treatment. The trial sites had naturally occurring populations of weeds. The weed spectrum included, but was not limited to, wild oat (*Avena fatua*, AVEFA); Shepherd's purse (*Capsella bursa-pastoris*, CAPBP); common lambsquarter (*Chenopodium album*, CHEAL); barnyardgrass (*Echinochloa crus-galli*, ECHCG); ryegrass (*Lolium* spp., LOLSS); short-spiked canarygrass (*Phalaris brachystachys*, PHABR); awned canarygrass (*Phalaris paradoxa*, PHAPA); narrow-leaved plantain (*Plantago lanceolata*, PLALA); annual blackgrass (*Poa annua*, POAAN); and wild buckwheat (*Polygonum convolvulus*, POLCO).

Treatments consisted of tank mixes of penoxsulam and pyroxsulam or pyroxsulam+cloquintocet (mexyl) applied in water. Where used, Actirob B adjuvant was applied at use rate of 0.2 to 1 liter per hectare (L/ha) with pyroxsulam containing treatments and in tankmixes. Penoxsulam was applied using the commercial formulation Viper/Boa which contains a built-in adjuvant at a rate of 0.7 liters per 20 grams active ingredient (ai). Pyroxsulam was applied using 15% to 25% WP formulations, with cloquintocet (mexyl) applied at a maximum rate of 18.75 gr ai/ha. Formulated products were used to make the single and tank-mix treatments. The application volumes were between 200 to 250 L/ha. All application were made using precision gas hand sprayers using a 2 to 2.5 m boom using flat fan (80° or 110°) nozzles to broadcast the treatments on the soil.

Evaluation

The treated plots and control plots were rated blind at various intervals after application. Ratings were based of Percent (%) Visual weed control, where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected}=A+B-(A\times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 1-3. All comparisons are an average of 2 to 4 replicates and are significant at the P>0.05 level.

Tables

TABLE 1

Control of CAPBP, CHEAL, ECHCG and POLCO by Penoxsulam plus Pyroxsulam at 39-51 Days After Application in the field.

| Pyroxsulam | Penoxsulam | CAPBP | | CHEAL | | ECHCG | | POLCO | |
|---|---|---|---|---|---|---|---|---|---|
| (rate in grams ai/ha) | | Obs | Exp* | Obs | Exp* | Obs | Exp* | Obs | Exp* |
| 4 | 0 | 70 | — | 65 | — | 65 | — | 35 | — |
| 0 | 5 | 20 | — | 10 | — | 0 | — | 50 | — |
| 4 | 5 | 100 | 75 | 91 | 69 | 94 | 65 | 85 | 68 |

CAPBP = Shepherd's purse (*Capsella bursa-pastoris*)
CHEAL = common lambsquarter (*Chenopodium album*)
ECHCG = barnyardgrass (*Echinochloa crus-galli*)
POLCO = wild buckwheat (*Polygonum convolvulus*)
Obs = Observed Response
Exp* = Expected Response

TABLE 2

Control of AVEFA, PHABR and PHAPA by Penoxsulam plus Pyroxsulam at 28 to 56 Days After Application in the field.

| Pyroxsulam | Penoxsulam | AVEFA | | PHABR | | PHAPA | |
|---|---|---|---|---|---|---|---|
| (rate in grams ai/ha) | | Obs | Exp* | Obs | Exp* | Obs | Exp* |
| 18 | 0 | 65 | — | 38 | — | 80 | — |
| 0 | 20 | 0 | — | 0 | — | 0 | — |
| 18 | 20 | 80 | 65 | 59 | 38 | 95 | 80 |

AVEFA = wild oat (*Avena fatua*)
PHABR = short-spiked canarygrass (*Phalaris brachystachys*)
PHAPA = awned canarygrass (*Phalaris paradoxa*)
Obs = Observed Response
Exp* = Expected Response

TABLE 3

Control of LOLSS, PLALA and POANN by Penoxsulam plus Pyroxsulam at 14 to 61 Days After Application in the field.

| Pyroxsulam | Penoxsulam | LOLSS | | PLALA | | POANN | |
|---|---|---|---|---|---|---|---|
| (rate in grams ai/ha) | | Obs | Exp* | Obs | Exp* | Obs | Exp* |
| 20 | 0 | 0 | — | 7 | — | 0 | — |
| 0 | 20 | 20 | — | 13 | — | 17 | — |
| 20 | 20 | 65 | 20 | 57 | 18 | 50 | 17 |

LOLSS = ryegrass (*Lolium* spp.)
PLALA = narrow-leaved plantain (*Plantago lanceolata*)
POANN = annual blackgrass (*Poa annua*)
Obs = Observed Response
Exp* = Expected Response

What is claimed is:

1. A synergistic herbicidal mixture comprising a herbicidally effective amount of (a) penoxsulam and (b) pyroxsulam, wherein the weight ratio of penoxsulam to pyroxsulam is from about 1:1 to about 1.25:1, and the herbicides consist of penoxsulam and pyroxsulam.

2. An herbicidal composition comprising an herbicidally effective amount of the synergistic herbicidal mixture of claim 1 and an agriculturally acceptable adjuvant and/or carrier.

3. A method of controlling undesirable vegetation which comprises contacting the undesirable vegetation or the locus thereof with, or applying to the soil to control the emergence or growth of the undesirable vegetation, a herbicidally effective amount of the synergistic herbicidal mixture of claim 1.

4. A method for controlling undesirable vegetation in rice, cereal and grain crops, tree and vine crops, pome, stone and citrus crops, pastures, rangelands, industrial vegetation management (IVM), and turf, which comprises contacting the undesirable vegetation or the locus thereof with, or applying to the soil to control the emergence or growth of the undesirable vegetation, a herbicidally effective amount of the synergistic herbicidal mixture of claim 1.

* * * * *